United States Patent [19]

Schumann

[11] Patent Number: Plant 7,393

[45] Date of Patent: Dec. 11, 1990

[54] GERANIUM PLANT NAMED FISCAB

[75] Inventor: Ingeborg Schumann, Hoehr-Grenzhausen, Fed. Rep. of Germany

[73] Assignee: Florfis AG, Binningen, Switzerland

[21] Appl. No.: 426,154

[22] Filed: Oct. 25, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of Geranium plant named Fiscab, particularly characterized by the combined features of orange-red semi-double flowers, rich flowering, dark foliage, vigorous growth, fast rooting, good heat tolerance, and good tolerance to shipping.

1 Drawing Sheet

The present invention comprises a new and distinct cultivar of Geranium, botanically known as *Pelargonium zonale,* and hereinafter referred to by the cultivar name Fiscab.

Fiscab is a product of a planned breeding program which had the objective of creating new Geranium cultivars with dark foliage, good growth habit, orange-red flower color, and perhaps in other ways improving the commercial cultivar Cararet. Cabaret is disclosed in U.S. Plant Pat. No. 5,992.

Fiscab was originated from a hybridization made by the inventor in a controlled breeding program in Galdar, Gran Canaria, Spain, in 1983.

The female parent was an inbred line of the cultivar Westfalenstar, characterized by its orange-red color, semi-double flowers, but inferior branching. The male parent of Fiscab was a hybrid resulting from the cross of an unnamed male cultivar (I4 Adonis × Bernzo), and the female cultivar Snow Cap. Adonis was selected for its single red flowers, Bernzo for its single orange-red flowers and dark leaves, and Snowcap is characterized by its white semi-double flowers.

Fiscab was discovered and selected as one flowering plant within the progeny of the stated cross by Ingeborg Schumann in May 1984 in a controlled environment in Hillscheid, Federal Republic of Germany.

The first act of asexual reproduction of Fiscab was accomplished when vegetative cuttings were taken from the initial selection in February 1985 in a controlled environment in Hillscheid, Federal Republic of Germany by, or under the supervision of, Ingeborg Schumann.

Horticultural examination of selected units initiated in Spring 1985 and continuing thereafter has demonstrated that the combination of characteristics as herein disclosed for Fiscab are firmly fixed and are retained through successive generations of asexual reproduction.

Fiscab has not been observed under all possible environmental conditions. The phenotype may vary significantly with variations in environment such as temperature, light intensity and daylength.

The following observations, measurements and comparisons describe planes grown in Hillscheid, Federal Republic of Germany, under greenhouse and outdoor conditions which approximate those generally used in commercial practice.

The following traits have been repeatedly observed and are determined to be basic characteristics of Fiscab, which, in combination, distinguish this Geranium as a new and distinct cultivar:

1. Bright orange-red flowers.
2. Very floriferous habit.
3. Dark green foliage which ships well.
4. Vigorous growth.
5. Fast rooting.
6. Excellent tolerance to heat.

Of the many commercial cultivars known to the present inventor, the most similar in comparison to Fiscab is the cultivar Cabaret. Reference is made to attached Chart A which compares certain characteristics of Fiscab to those same characteristics of Cabaret. In general comparison to Cabaret, Fiscab has better branching, more vigorous growth, better flower production, a brighter, more orange flower color on the upper surface of the petals, and a distinctly different, more reddish color on the under surfaces of the petals.

The accompanying color photographic drawing shows typical flower and foliage characteristics of Fiscab, with the colors being as true as possible with illustrations of this type.

In the following description color references are made to The Royal Horticultural Society Color Chart (RHS) and in certain instances to the Horticultural Color Chart (HCC). The color values were determined between 2:00 p.m. and 3:00 p.m. indoors on May 6, 1988 under 48,000 Lux light intensity at Hillscheid, Federal Republic of Germany.

Classification:

*Botanical.*—A hybrid of the genus *Pelargonium zonale* l'hert. cv Fiscab.

*Commercial.*—Zonal geranium.

INFLORESCENCE

A. Umbel:

*Average diameter.*—Indoor, 9.4 cm; outdoor, 9.7 cm.

*Average depth.*—Indoor, 4.8 cm; outdoor, 4.4 cm.

*Peduncle length.*—Indoor, 13.0 cm; outdoor, 15.0 cm.

*Pedicel length.*—Indoor, 2.5 cm; outdoor, 2.3 cm.

B. Corolla:

*Average diameter.*—Indoor, 4.7 cm; outdoor, 4.7 cm.

*Form.*—Semi-double.

*Color (general tonality from a distance of three meters).*—Orange, RHS 43B; HCC 719/1-2.

*Color (upper surface, main body and margin).*—RHS 43B; HCC 719/1-2.

*Color (under surface).*—RHS 47C, HCC 620, with lighter, almost white spots.

*Sepals.*—Green.

*Pedicels.*—Light red.

C. Bud:

*Shape.*—Elliptic.

*Color.*—Green.

*Pedicels.*—Green, turning red after opening of the buds.

D. Reproductive organs:

*Androecium.*—7–9 anthers.

*Gynoecium.*—5 lobed stigma.

E. Spring flowering response period: In Hillscheid, Federal Republic of Germany in 1988, 80% of plants with at least 1 flower opened 12 weeks after planting of unrooted cuttings in week 5.

F. Outdoor flower production: The flower count in 1988 in Hillscheid, Federal Republic of Germany indicated between 55 and 60 flowers per plant for June through October observation period.

G. Durability: Good rain resistance, good heat tolerance.

PLANT

A. Foliage:

*Form.*—Nearly round, semi-double.

*Margin.*—Bicrenate.

*Color.*—Medium to dark green.

*Zonation.*—Weak brown zonation.

*Tolerance to botrytis.*—Very good.

B. General appearance and form:

*Internode length.*—Short.

*Branching pattern.*—4.0 branches per plant after 13 weeks of growing time from unrooted cuttings.

*Height.*—26 cm on average.

CHART A

COMPARISON OF FISCAB AND CABERET

| | FISCAB | CABARET |
|---|---|---|
| Flower color | orange-red (RHS 43B) | orange-red (RHS 43C) |
| Color of lower side | Pale orange (RHS 47C) with white spots | orange-red (RHS 43C) |
| Pedicel length | 2.5 cm | 3.3 cm |
| Peduncle length | 13.0 cm | 17.5 cm |
| Branching habit (number of branches) | 4.0 | 3.2 |
| Corolla diameter | 4.7 cm | 5.0 cm |
| Number of umbels | 55–60 | 45 |
| Diameter of umbel | 9.5 cm | 11.5 cm |

I claim:

1. A new and distinct cultivar of Geranium plant named Fiscab, as illustrated and described.

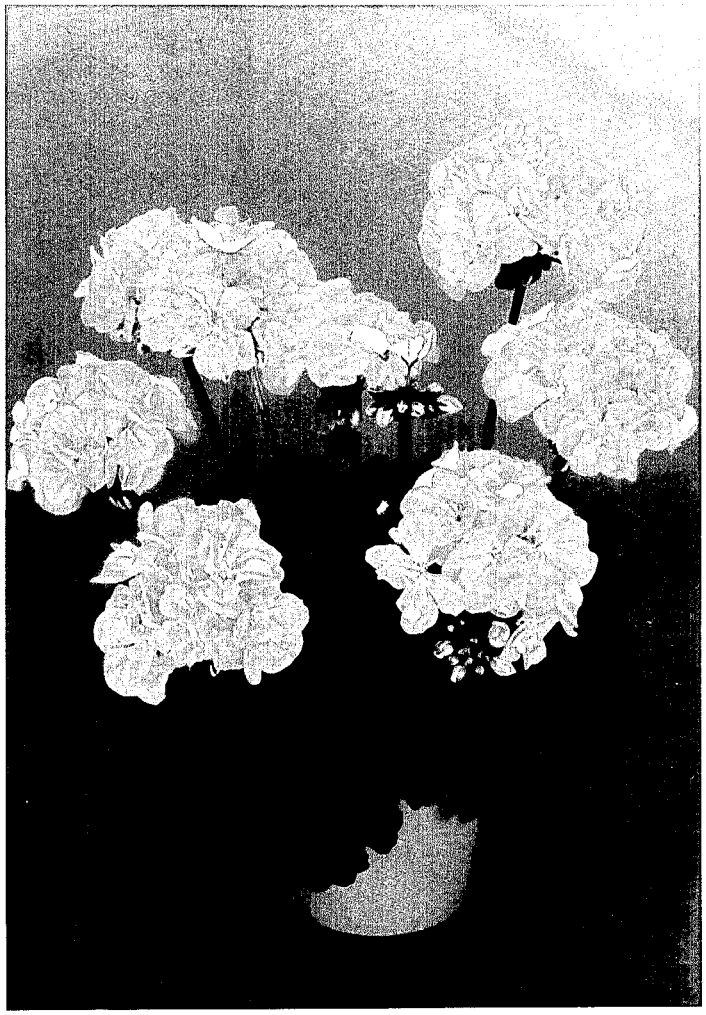

* * * * *